(12) United States Patent
Tang et al.

(10) Patent No.: US 7,131,446 B2
(45) Date of Patent: Nov. 7, 2006

(54) LIGHT-TRIGGERED TATTOO PROCESS

(76) Inventors: Kenneth Y. Tang, 2729 Via Asoleado, Alpine, CA (US) 91901; Allen M. Hunter, II, 316 Pualoa Nani Pl., Kihei, HI (US) 96753; Betty W. Tang, 2729 Via Asoleado, Alpine, CA (US) 91901

( * ) Notice: Subject to any disclaimer, the term of this patent is extended or adjusted under 35 U.S.C. 154(b) by 477 days.

(21) Appl. No.: 10/810,778

(22) Filed: Mar. 25, 2004

(65) Prior Publication Data
US 2005/0234528 A1    Oct. 20, 2005

(51) Int. Cl.
*A61B 19/00* (2006.01)
(52) U.S. Cl. ............................. 128/898; 607/88; 606/9
(58) Field of Classification Search .................. 606/8, 606/9; 607/88–91; 128/898
See application file for complete search history.

(56) References Cited

U.S. PATENT DOCUMENTS

| 4,493,869 | A | * | 1/1985 | Sweeny et al. ............. 428/201 |
| 5,817,089 | A | * | 10/1998 | Tankovich et al. ............. 606/9 |
| 5,988,174 | A | * | 11/1999 | Chasan ......................... 128/898 |
| 6,013,122 | A | * | 1/2000 | Klitzman et al. ......... 106/31.03 |
| 6,162,211 | A | * | 12/2000 | Tankovich et al. ............. 606/9 |
| 6,470,891 | B1 | * | 10/2002 | Carroll ........................ 128/897 |
| 6,800,122 | B1 | * | 10/2004 | Anderson et al. ......... 106/31.03 |
| 6,814,760 | B1 | * | 11/2004 | Anderson et al. ............... 8/404 |
| 6,881,249 | B1 | * | 4/2005 | Anderson et al. ......... 106/31.03 |
| 2001/0023328 | A1 | * | 9/2001 | Felton et al. .................. 602/41 |

* cited by examiner

*Primary Examiner*—A. Farah
(74) *Attorney, Agent, or Firm*—John R. Ross (57) ABSTRACT

A light-triggered tattoo process. A strong absorber of light energy and tattoo material are sandwiched under pressure between a skin region and a transparent window. Short pulses of light, at frequencies strongly absorbed by the strong absorber, illuminates the strong absorber through the window creating micro-explosions in the strong absorber that drive particles of the tattoo material into the skin region producing a tattoo.

24 Claims, 6 Drawing Sheets

TRANSPARANCY
GRAPHITE PARTICLES
COLOR INK PARTICLES
(RED, YELLOW, GREEN, BLUE, ETC.)

FIG. 5

COLOR PARTICLES
GRAPHITE PARTICLES
TRANSPARANCY
GLASS COVER

LIGHT-TRIGGERED TATTOO PROCESS

BACKGROUND OF THE INVENTION

Humans have been applying tattoos to the skin for over 8000 years. The inks and dyes used were historically derived from substances found in nature and comprise a heterogeneous suspension of pigmented particles and other impurities. A well-known example is India ink, a suspension of carbon particles in a liquid.

Tattoos are typically produced by applying, with tattoo needles, tattoo ink into the dermis, where the ink remains permanently. This technique introduces the pigment suspension through the skin by an alternating pressure-suction action caused by the elasticity of the skin in combination with the up-and-down movement of the tattoo needles. Water and/or other carriers for the pigment introduced into the skin diffuse through the tissues and are absorbed. The insoluble pigment particles remain in the dermis where they were initially placed, for the most part. Inks used for tattooing resist elimination by virtue of their inertness and the relatively large size of the insoluble pigment particles. A tattoo produced in this manner will partially fade over time but will generally remain present throughout the life of the tattooed person.

Tattoos are used for a variety of reasons, primarily for ornamentation of the skin. While tattoos have traditionally been applied as designs for the skin, they are also used for permanent cosmetics, such as eyeliner and lip color often by people who cannot apply makeup, such as those suffering from arthritis or Parkinson's disease. Additionally, for breast reconstruction after mastectomy, it is desirable to reconstruct the nipple and areola area with darker flesh tone tattooing in order to produce a natural-looking breast. Moreover, tattooing has been used to treat hypo- and hyper-pigmentation caused by vitiligo, skin grafts, port-wine stains, and other dermatologic conditions.

Quite often people have a change of heart after being tattooed. For example, a person may desire to remove or change the design of a decorative tattoo, such as the name of an old girl friend after the tattooed persons marries someone else. Alternatively, an individual with cosmetic tattooing, such as eyeliners, eyebrows, or lip coloring, may wish to change the color or area tattooed as fashion changes. In addition, following breast reconstruction, the geometry of the breast may change over time, leading to a tattooed nipple changing from an aesthetically pleasing position to an unpleasant one.

Unfortunately, there is currently no simple and completely successful way to remove tattoos. Removal by surgical excision, dermabrasion, requires invasive procedures associated with potential complications, such as infections, and usually results in conspicuous scarring. Removal by laser therapy is the most common technique and is usually limited to eliminating only from 50–70% of the tattoo pigment, resulting in a residual smudge. Laser removal requires multiple treatment sessions (usually five to twenty) with expensive equipment for maximal elimination. Thus, the overall cost of laser removal is generally prohibitively expensive for many people. Additionally, most tattooing inks are made of pigments which have a wide range of particle size. If the pigment particles are small, they may diffuse through the tissues, causing "bleeding" of the color, "blurring" of the lines of the tattoo, or partial fading of the tattoo.

Prior art temporary substitutes for tattoos are unsatisfactory because they tend to be very short-lived. If only the surface of the skin is colored, such as by painting on the skin, the ornamentation is easily removed by wetting or rubbing the skin or by the natural sloughing of epidermis every three to four weeks. While this technique produces only temporary skin ornamentation, it would be desirable to have the option to color the skin to last longer than a few hours, days, or weeks.

Figure 1:
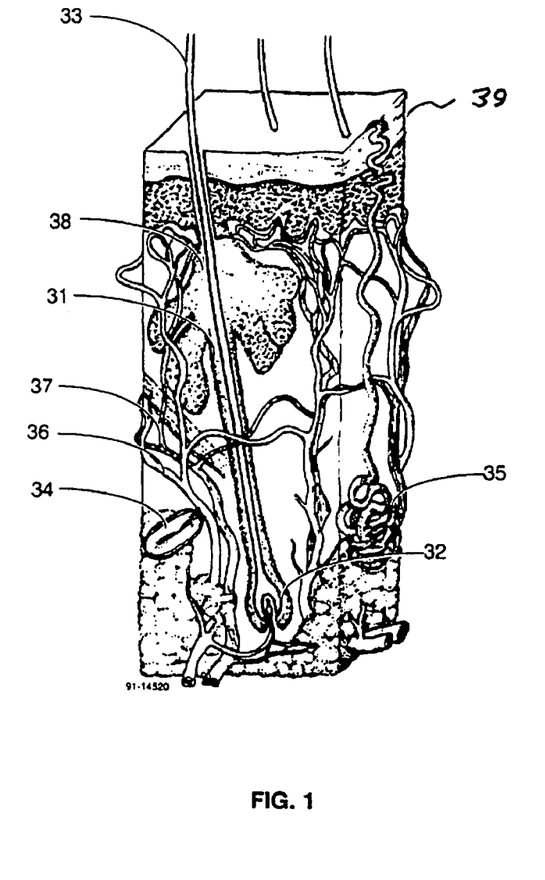
FIGS. 1 and 1A show the composition of human skin.
Figure 1A:
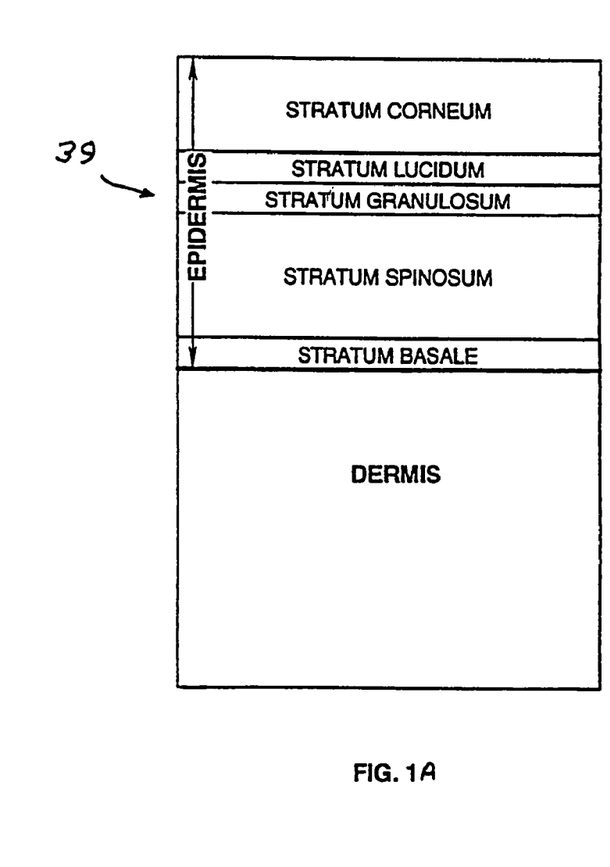

The epidermis, 39 in FIG. 1 and FIG. 1A of the human skin comprises several distinct layers of skin tissue. The deepest layer is the stratum basale layer which consists of columnar cells. The next layer up is the stratum spinosum composed of polyhedral cells. Cells pushed up from the stratum spinosum are flattened and synthesize keratohyalin granules to form the stratum granulosum layer. As these cells move outward they lose their nuclei and the keratohyalin granules fuse and mingle with tonofibrils. This forms a clear layer called the stratum lucidum. The cells of the stratum lucidum are closely packed. As the cells move up from the stratum lucidum they become compressed into many layers of opaque squamas. These flattened cells have become completely filled with keratin and have lost all other internal structure, including nuclei. These squamas constitute the outer layer of the epidermis, the stratum corneum. At the bottom of the stratum corneum the cells are closely compacted and adhere to one another strongly, but higher in the stratum they become loosely packed and eventually flake away at the surface. Also shown in FIG. 1 is hair stem 33 sebaceous gland 38, hair duct 31, nerve ending 34, veins and arteries 36 and 37, sweat gland 35 and pupilla 32.

It is known that graphite vaporizes at about 3,600.degrees. C. It is known that graphite is a strong absorber of infrared light and that infrared light such as the 1.06 micron laser beam produced by the Nd:YAG laser will penetrate several millimeters through human skin. It is also known that short pulses of light energy absorbed by a strongly absorbing material can result in shock waves creating mechanical forces.

What is needed is a better method for applying tattoo quickly and without needles and pain.

SUMMARY OF THE INVENTION

The present invention provides a light-triggered tattoo process. A strong absorber of light energy and tattoo material are sandwiched under pressure between a skin region and a transparent window. Short pulses of light, at frequencies strongly absorbed by the strong absorber, illuminates the strong absorber through the window creating micro-explosions in the strong absorber that drive particles of the tattoo material into the skin region producing a tattoo.

In a preferred embodiment the strong absorber is small particles of graphite, such as the graphite particles in India ink. The graphite is printed on a transparent substrate such as an overhead transparency. A thin layer of tattoo material is applied over the graphite particles. The transparent substrate is pressed firmly against a skin region with the tattoo material and the graphite particles sandwiched between the skin and the transparency. The transparency functions as the window. Pulsed laser beams are directed through the transparent substrate and absorbed by the graphite to produce thousands of micro-explosions in the graphite and the explosions drive tattoo material into the epidermis layers of the skin. In preferred embodiments the tattoo material may be printer color ink. For black portions of tattoos the tattoo material can be the same graphite particles functioning as the strong absorber.

Very high quality tattoo patterns can be prepared quickly and easily using modern color printer/copiers. The tattoos can be applied safely to the skin of a patient in a matter of a few minutes or even seconds with no pain. In these preferred embodiments a glass plate may be applied on top of the transparency substrate to provide uniform pressure in the region between the substrate and the skin. In this case both the glass plate and the transparency functions as the window. A preferred light source is a Nd-YAG laser operating at a 1.06 micron wavelength with short pulses in the range of a 100 to 300 microseconds with repetition rates up to a few hundred Hz. Shorter pulses in the range of a few nano-seconds can also be utilized, but care must be taken to control the pulse energy so that the tattoo material is not vaporized. Many other short pulse light sources could be utilized including a wide variety of short pulse lasers and flash lamps, such as xenon flash lamps. Tattoos in preferred embodiments are limited to depths of about 100 to 200 microns in the epidermis and are not permanent. In addition, if desired, they can be quickly removed using a variety of techniques such as the same Nd-YAG laser operating at increased power density.

DETAILED DESCRIPTION OF PREFERRED EMBODIMENTS

Applicants discovered some time ago that when small particles of graphite are illuminated with very short pulses of laser light of sufficient energy the individual particles explode violently. If the pulse-duration and energy is chosen correctly graphite particles in the sub-micron size range will violently break apart into smaller fragments. Subsequent pulses continue to break the particles into even smaller sizes until the particles disappear. For example, in an inert atmosphere after repeated illumination with 1.06 micron, 12 nanoseconds, 3 Joules per $cm^2$ pulses, the particles are broken into extremely small particles barely visible to the unaided eye. But in air the particles after such repeated illumination disappear completely, apparently forming $CO_2$.

The present invention utilizes the micro-explosive force (created by the partial or complete vaporization of small particles due to the absorption of light energy in very short time intervals) to force black and/or color ink particles into the epidermis region skin tissue.

First Embodiment—Color Application

A first preferred embodiment of the present invention can be described by reference to FIGS. 2 through 8.

Figure 2:
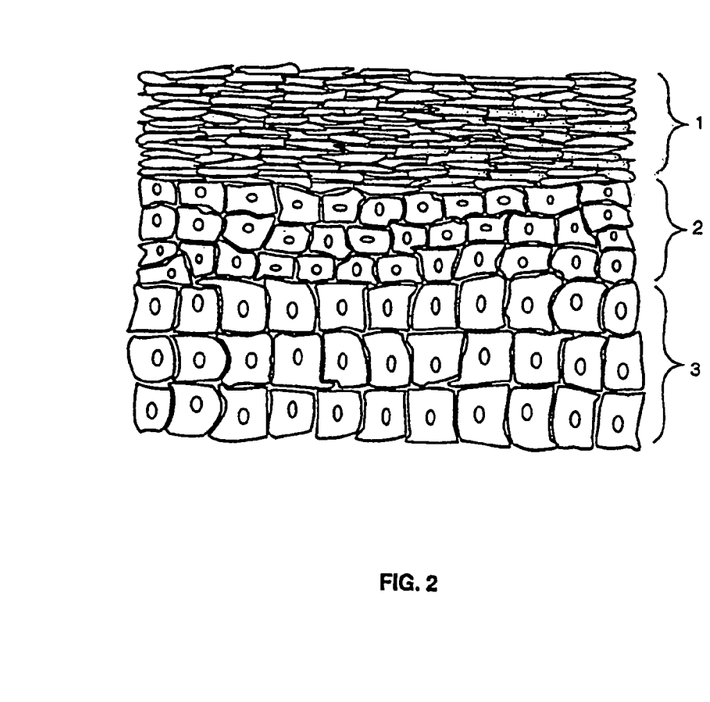
FIG. 2 shows layers of the epidermis.

FIG. 2 shows layers of the epidermis as discussed in the Background section. The epidermis is typically a few hundred microns thick. The purpose of the present invention is to deposit beautiful color patterns in the epidermis region of the skin quickly and painlessly using lasers to produce micro explosions to drive the tattoo ink into this region of the skin.

Figure 3:
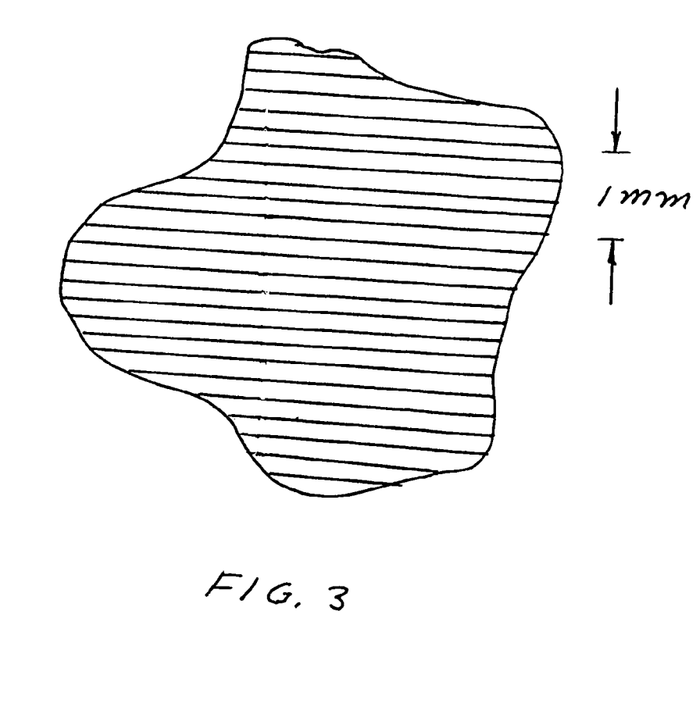
FIG. 3 shows how black ink (comprised of graphite particles) is applied to a transparency by a modern color printer to produce a gray color.
Figure 4:
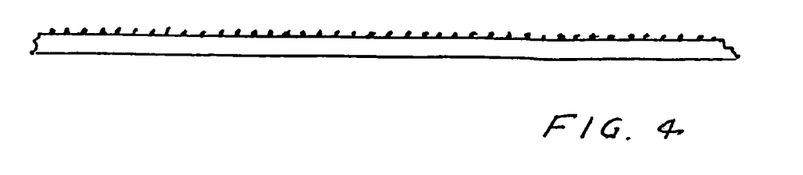
FIG. 4 shows a cross section of a gray transparency with rows of graphite particles.
Figure 5:
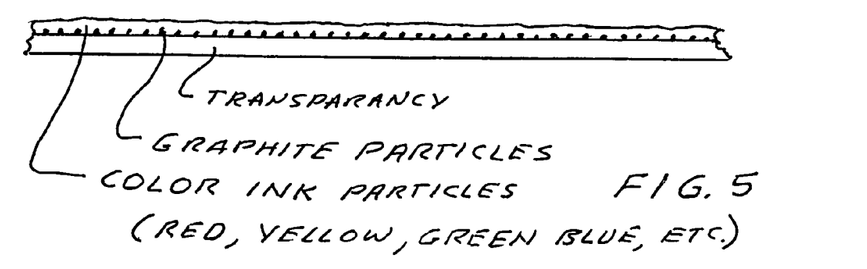
FIG. 5 shows the gray transparency with a layer of color (such as red) ink covering the graphite rows.
Figure 6:
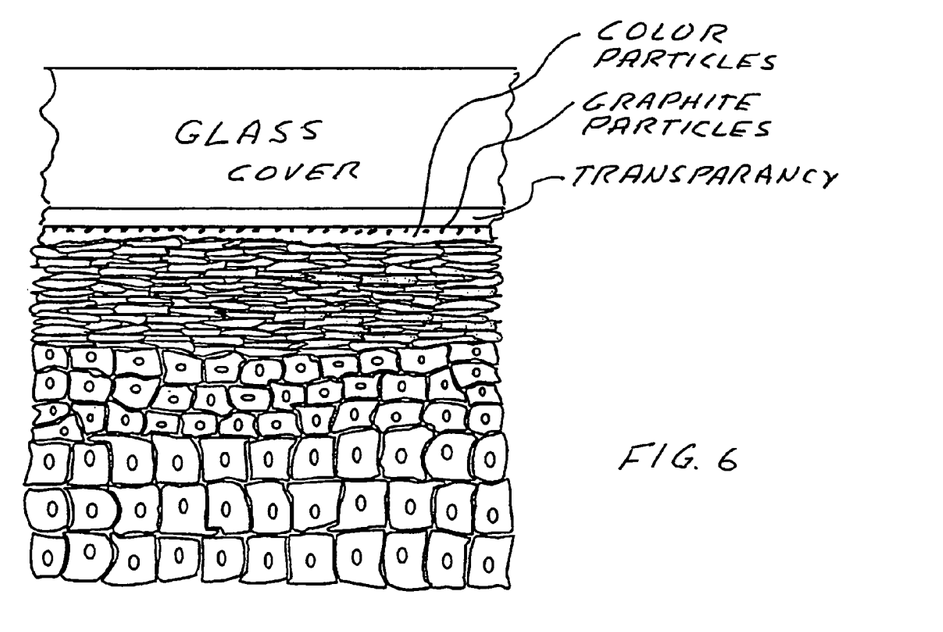
FIG. 6 shows a setup in preparation to applying a color tattoo.
Figures 6A, 7:
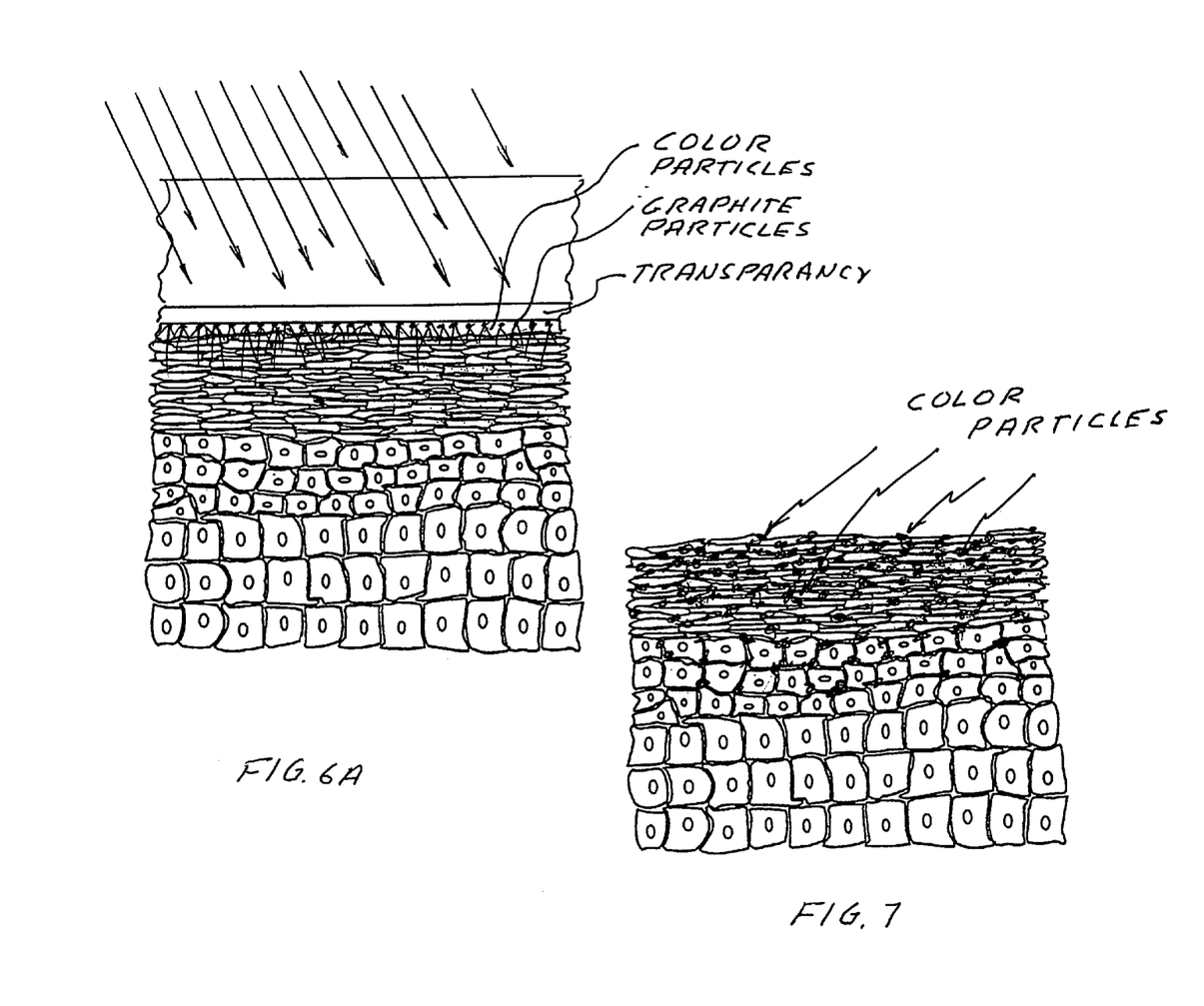
FIG. 6A shows graphite particles exploding to force color ink into the epidermis region of the skin.
FIG. 7 shows color particles distributed in the epidermis.
Figure 8:
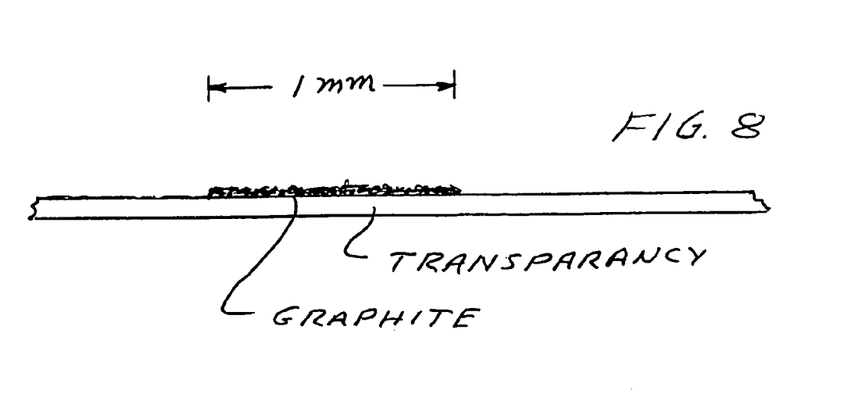
FIG. 8 shows a cross section of a transparency with a 1 mm wide black line printed on it.

In this embodiment a color printer/copier is used to prepare a color tattoo pattern. FIG. 3 shows how black ink (comprised of graphite particles) is applied to a transparency (such as Xerox laser/copier transparencies, Model 3R3108) by a modern color printer to produce a gray color. In a modern color printer/copier such as the Xerox Docucolor 12, colors are laid down in rows as shown in FIG. 3. Applicants count 5 rows per millimeter, so that the rows are on 200 micron centers. Dark to light control is produced by making the lines thicker. At the dark setting the lines tend to meet and blur together to produce a solid pattern. The pattern shown in FIG. 3 would correspond to a light setting. If the printer/copier is set to black and white, the rows are produced with black printer ink that is basically small graphite particles. As indicated above these small graphite particles explode when illuminated with very short pulses of laser infrared light at (for example) a wavelength of 1.06 micron. FIG. 4 shows a cross section of a gray transparency with rows of graphite particles. Next a color pattern is copied over the graphite rows on the transparency. FIG. 5 shows the gray transparency with a layer of color (such as red) ink covering the graphite rows. Next the transparency is placed on the skin to be tattooed with the color layer sandwiched between the skin and the transparency. And a glass plate is placed over the transparency to apply pressure on the skin to hold the color layer tightly against the skin. FIG. 7 shows the setup in preparation to applying a color tattoo. The layer is then illuminated with short pulses of the laser light to explode the graphite particles. Applicants' best results using an Nd-YAG laser were with 300 micro-second pulse-width pulses operating at 250 Hz. The spot size was only about 1.0 mm so the beam had to be scanned rapidly so as to not produce spot heating. FIG. 7A shows graphite particles exploding to force color ink into the epidermis region of the skin. FIG. 8 shows the result of the procedure with the color particles distributed in the epidermis. Prototype tests were performed with animal skin similar to human skin. Microscopic examination of the skin showed that the particles penetrated to about 150 microns into the skin. None of the tattoo ink would rub off with normal rubbing. To tattoo a pattern of one square centimeter onto the skin of a client could be done in about 10 seconds.

Second Embodiment—Black Patterns

Figure 9:
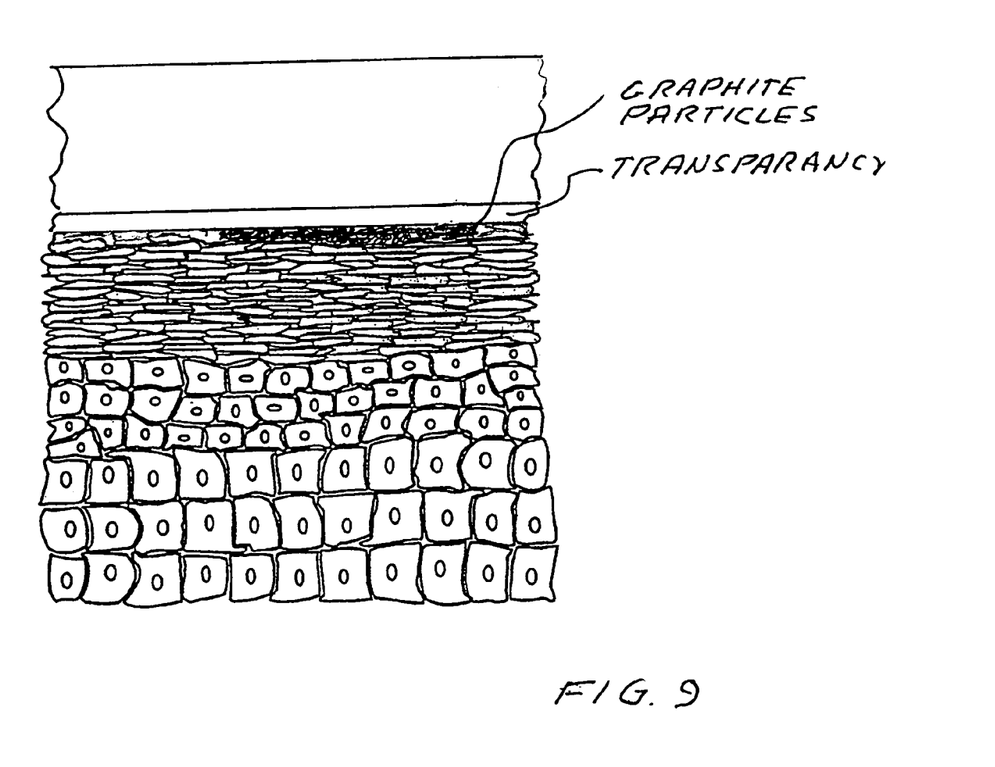
FIG. 9 shows a setup in preparation for a black line tattoo.
Figure 9A:
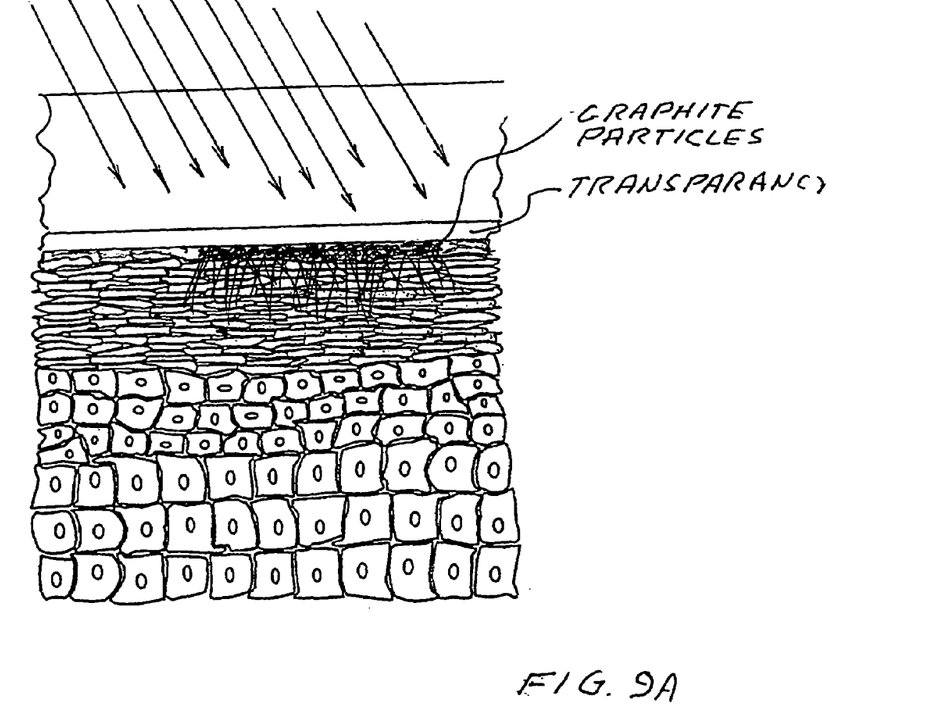
FIG. 9A shows graphite particles exploding to force graphite particles into the epidermis region of the skin.
Figure 10:
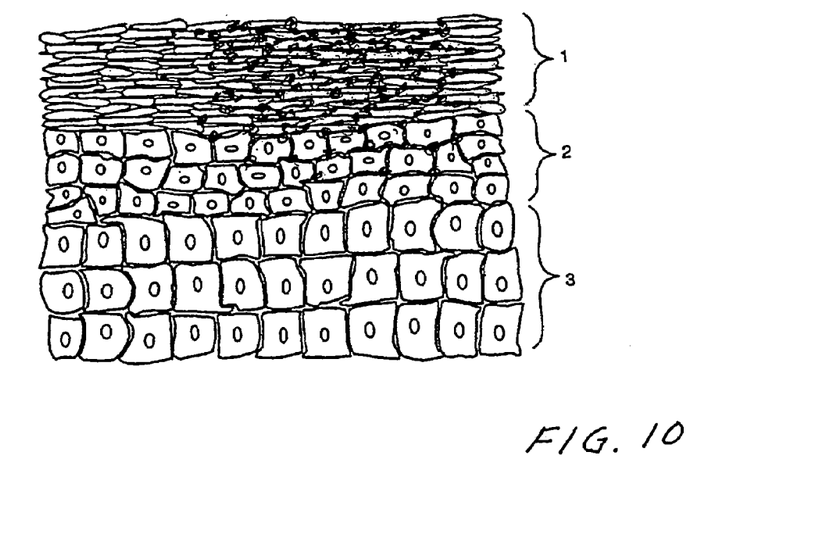
FIG. 10 shows the graphite distributed in the epidermis.

A second technique for producing black tattoo patterns is shown with FIGS. 8 through 10. In this embodiment, relatively thick black lines are printed on transparencies using the same equipment as described above. The normal settings of the printer/copier provide adequate results. The cross section of a single line, such as the cross section of an "I" that is about 1 mm wide and maybe 50 graphite particle high is shown in FIG. 8. The tattoo could be a short phrase such as "NANCY MY LOVE" or a black outline pattern. The mirror image of the letters should be printed on the transparency. FIG. 9A shows the illumination step that is the same as above. In this case some of the graphite particles explode driving other particle into the skin. Excellent tattoos were produced with particles driven about 150 microns into the skin.

Explosive Graphite

Graphite is very absorptive of laser energy at the 1.06 micron wavelength. The latent heat of vaporization is about $10^5$ J/cm$^3$ for cold solid graphite. (The energy required to heat room temperature graphite to the sublimation temperature is roughly 4% of the sublimation energy.) Thus, to vaporize a 1 micron cube ($10^{-12}$ cm$^3$) would require approximately $10^{-7}$ J. The energy falling on the surface of the 1 micron particle ($1 \times 10^{-8}$ cm$^2$) in a 3 J/cm$^2$ pulse is $3 \times 10^{-8}$ J, about one third of the energy needed to totally vaporize the particle. Therefore, a significant portion of the particle is vaporized. The energy is deposited too quickly for the heat to diffuse; therefore, the particle explodes violently upon being illuminated by the short-duration pulse. (Subsequent pulses will vaporize the smaller particles created by the earlier pulses.) The resulting forces of the tiny explosions forces a portion of the ink into the skin tissue.

OTHER TECHNIQUES AND EMBODIMENTS

The two examples described above are experiments actually performed to prove the feasibility of the present invention. Persons skilled in the arts to which this invention relates will recognize that there are many other ways to practice the present invention.

Other Light Sources

For example, numerous other lasers and wavelengths and could be utilized. In fact any technique that employees a material capable of producing micro-explosions upon illumination with very short pulsed of light to produce tattoos in the skin could be substituted for the techniques described above. This includes lasers operated with pulse durations of a few nanoseconds. Care should be taken however to tailor the pulses so that they do not vaporize the colors. Short pulse flash lamps can also be used as the light source. A good choice would be a xenon flash lamp.

Other Strong Absorbers

Many particles in addition to graphite will explode upon illumination with short laser pulses. Particles chosen, however, must have a high absorption at the wavelength of the laser chosen.

Other Tattoo Materials

The tattoo material, of course, could be tattoo ink. By matching a particular color ink to a light source highly absorbent in that ink, the ink itself can function as the strong absorber so that portions of the ink undergoes micro-explosions to drive other portions of that color into the skin. This technique is basically the technique described in the second preferred embodiment where small graphite particles function both as the absorber and the tattoo material.

Other Sandwich Techniques

Other techniques for sandwiching the strong absorber and the tattoo material between the window and the skin could be used. Instead of the printer/copier referred to in the description of the first embodiment an inkjet printer could be used to print the tattoo patterns on transparencies. In this case tattoo ink can be used in the inkjet printer (perhaps with some modifications to the printer). Instead of printing the absorber and the tattoo material on the transparent substrate (window), the tattoo material could be painted on the skin as a tattoo pattern and a strong absorber (such as India ink) could be sprayed over the pattern. A glass window could be pressed over the graphite sprayed pattern and the pattern could then be illuminated to produce tattoos similar to those described above. Alternative, the tattoo pattern could be painted on the skin and the graphite printed on a transparency as shown in FIG. 3. With a glass plate a sandwich could then be made to create a sandwich that looks the same as the one shown in FIG. 6.

Control Techniques

The present invention presents several opportunities to control various qualities of the tattoos produced. For example, the depth of the particle penetration can be controlled to various extents through variations of pulse energy, pulse duration, choice of strong absorber (e.g., graphite), density of absorber, pressure applied to the window against the skin region.

USES OF THE INVENTION

Applicants expect that the present invention will applied for all or substantially all of the uses to which conventional tattoos are now applied such as tattoos for skin decoration. However, since the present process is so quick, so simple, so safe, so painless and temporary, Applicants believe that its use will be far more extensive than conventional tattoo processes. A lady can have a facial make-over that will have a completely natural look in a few minutes that will last for weeks or months (instead of hours). A skin tan can be applied quickly that may last all winter. It should be feasible to tattoo an ink that is highly absorbent in the ultraviolet to reduce the risk of sunburn or skin cancer. The invention can be practice by dermatologist using existing equipment now used for treatments such as hair removal (or tattoo removal!). Some embodiments of the invention may also be practiced in traditional or up-scale tattoo parlors.

Thus, the reader should not construe the above examples as limitations on the scope of the invention, but merely as exemplifications of preferred embodiments thereof. Those skilled in the art will envision many other possible variations are within its scope. Accordingly the reader is requested to determine the scope of the invention by the appended claims and their legal equivalents, and not by the examples which have been given.

We claim:

1. A light-triggered tattoo process comprising the steps of:
   A) sandwiching under pressure, between a skin region and a transparent window, a strong absorber of light energy and tattoo material,
   B) illuminating through said window said strong absorber with short pulses of light, at frequencies strongly absorbed by the strong absorber, to create micro-explosions in the strong absorber to drive particles of the tattoo material into the skin region to produce a tattoo.

2. The process as in claim 1 wherein the strong absorber comprises graphite.

3. The process as in claim 2 wherein the tattoo material comprises tattoo ink.

4. The process as in claim 2 wherein the tattoo material comprises graphite.

5. The process as in claim 1 wherein the short pulses of light are provided with a laser.

6. The process as in claim 5 wherein the laser is a Nd-YAG laser.

7. The process as in claim 1 wherein the short pulses of light are provided with a flash lamp.

8. The process as in claim 7 wherein the flash lamp is a xenon flash lamp.

9. The process as in claim 1 wherein said window comprises a transparency.

10. The process as in claim 9 wherein said strong absorber is printed on said transparency.

11. The process as in claim 9 wherein said tattoo material is printed on said transparency over said strong absorber.

12. The process as in claim 10 wherein the strong absorber is printed using a color printer/copier.

13. The process as in claim 10 wherein the strong absorber and the tattoo material is printed using a color printer/copier.

14. The process as in claim 9 wherein the window also comprises a glass plate that is used to press the transparency against the skin region.

15. A laser tattoo process comprising the steps of:
A) applying an explosive absorber of light energy on a transparent substrate,
B) applying a tattoo material on the transparent substrate over the explosive absorber,
C) pressing the substrate firmly against a skin region with the tattoo material and the explosive absorber sandwiched between the transparent substrate and the skin,
D) illuminating the explosive absorber with pulsed laser beams are directed through the substrate to produce thousands of micro-explosions in the explosive absorber to drive tattoo material into the epidermis layers of the skin.

16. The process as in claim 15 wherein the explosive absorber comprises graphite.

17. The process as in claim 16 wherein the tattoo material comprises tattoo ink.

18. The process as in claim 16 wherein the tattoo material comprises graphite.

19. The process as in claim 15 wherein the pulsed laser beams are provided with a Nd-YAG laser.

20. The process as in claim 15 wherein the substrate is a transparency and the explosive absorber and the tattoo material is applied using a printer.

21. The process as in claim 15 wherein the substrate is a transparency and the explosive absorber and the tattoo material is applied using a copier.

22. The process as in claim 15 wherein the substrate is a transparency and the explosive absorber and the tattoo material is applied using a printer/copier.

23. The process as in claim 15 wherein the substrate is a transparency and the explosive absorber and the tattoo material is applied using an ink jet printer.

24. The process as in claim 15 wherein a glass plate is used to press the substrate against the skin region.

* * * * *